United States Patent [19]

Terao et al.

[11] Patent Number: 4,533,554
[45] Date of Patent: Aug. 6, 1985

[54] QUINONE DERIVATIVES AND USE

[75] Inventors: Shinji Terao, Toyonaka; Mitsuru Shiraishi; Kaneyoshi Kato, both of Suita, all of Japan

[73] Assignee: Takeda Chemical Industries, Ltd., Osaka, Japan

[21] Appl. No.: 471,457

[22] Filed: Mar. 2, 1983

Related U.S. Application Data

[62] Division of Ser. No. 182,401, Aug. 26, 1980, Pat. No. 4,388,312.

[30] Foreign Application Priority Data

May 18, 1979 [JP] Japan .................... 54-61915
Sep. 12, 1979 [JP] Japan .................... 54-117771

[51] Int. Cl.³ .................... A61K 31/185; C07C 50/02
[52] U.S. Cl. .................... 514/464; 260/396 R; 514/613
[58] Field of Search .................... 260/396 R; 424/315, 424/324

[56] References Cited

U.S. PATENT DOCUMENTS

| | | | |
|---|---|---|---|
| 3,562,277 | 2/1971 | Hansen et al. | 544/431 |
| 3,728,362 | 4/1973 | Morimoto et al. | 260/396 R |
| 3,875,163 | 4/1975 | Zumin et al. | 424/250 |
| 3,931,257 | 1/1976 | Pawson | 260/410.9 R |
| 3,950,418 | 4/1976 | Bollag et al. | 424/250 |
| 3,957,836 | 5/1976 | Morimoto et al. | 260/396 R |
| 4,139,545 | 2/1979 | Morimoto et al. | 260/396 R |

OTHER PUBLICATIONS

Brocklehurst, "Adv. Drug Res.", vol. 5, 1970, pp. 109-113.
Hanna et al., "Nature", vol. 290, 1981, pp. 343-344.
Weiss et al., "Science", vol. 216, 1982, pp. 196-198.

*Primary Examiner*—Richard L. Raymond
*Assistant Examiner*—Raymond Covington
*Attorney, Agent, or Firm*—Wenderoth, Lind & Ponack

[57] ABSTRACT

New quinone derivatives of the formula

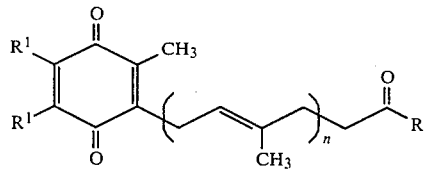

wherein $R^1$ is methyl or methoxy, or two of $R^1$ combine to represent $-CH=CH-CH=CH-$, R is amino which may be substituted or $-OR^4$ wherein $R^4$ is hydrogen, $C_{1-4}$ alkyl or $-(CH_2-CH=C(CH_3)-CH_2)_{\overline{m}}H$ (wherein m is an integer of 1 to 10), and n is an integer of 1 to 10 when R is amino which may be substituted, or n is an integer of 2 to 10 when R is $-OR^4$, and their hydroquinone forms, have useful physiological activities such as blood-pressure decreasing and antiallergic activities.

12 Claims, No Drawings

QUINONE DERIVATIVES AND USE

This application is a division of application Ser. No. 182,401, filed Aug. 26, 1980 (now U.S. Pat. No. 4,388,312).

The present invention relates to novel quinone derivatives which are of value as drugs or intermediates for them and to their production and use.

Fat-soluble vitamins such as vitamin E, vitamin K and ubiquinones exhibit physiological actions peculiar to their groups of compounds generally in the biomembrane, particularly in the phospholipid layer. The present inventors found that a group of compounds derived by converting into amides the terminals of (poly)prenyl side chains of these compounds exhibit excellent physiological activities, and, on the basis of the findings, have come to complete the present invention.

Thus, the compounds of the present invention are quinone derivatives of the formula:

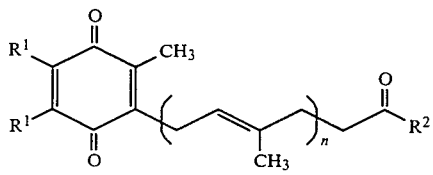

wherein n is an integer of 1 to 10; $R^1$ is methyl or methoxy, or two of $R^1$ combine to represent —CH=CH—CH=CH—; and $R^2$ is amino which may be substituted, and their hydroquinone forms.

The hydroquinone forms of the above-mentioned quinone compounds (Ia) are represented by the formula:

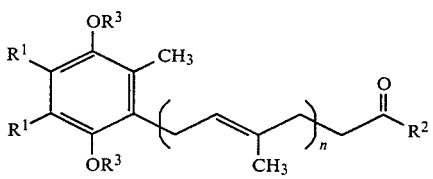

wherein n, $R^1$ and $R^2$ are as defined hereinbefore; and $R^3$ is hydrogen or a protective group.

With regard to the above-mentioned formulas (Ia) and (Ib), examples of the amino group which may be substituted include amino, mono- or di-substituted amino, cyclic amino, etc. As examples of such mono- or di-substituted amino group, there may be mentioned mono- or di-$C_{1-6}$alkylamino (e.g., methylamino, ethylamino, propylamino, isopropylamino, butylamino, isobutylamino, sec-butylamino, tert-butylamino, pentylamino, hexylamino, dimethylamino, diethylamino and methylethylamino), $C_{3-6}$cycloalkylamino (e.g., cyclopropylamino, cyclobutylamino, cyclopentylamino and cyclohexylamino), $C_{3-6}$cycloalkyl-$C_{1-3}$alkylamino (e.g., cyclopropylmethylamino and cyclobutylmethylamino), phenyl-$C_{1-3}$alkylamino (e.g., benzylamino, phenetylamino and α-methylbenzylamino), pyridyl-$C_{1-3}$alkylamino (e.g., 2-pyridylmethylamino, 3-pyridylmethylamino and 4-pyridylethylamino), $C_{1-4}$alkoxyamino (e.g., methoxyamino and ethoxyamino), anilino, hydrazino, phenylhydrazino, m-trifluoromethylphenylhydrazino, N,N-dimethylhydrazino, histamino, tryptamino, N,N'-dicyclohexylureido, 4-methyl-1-piperadinylamino, 5-(1H-tetrazolyl)amino, etc., while as examples of the cyclic amino group may be mentioned azetidinyl, pyrrolidinyl, piperazinyl, piperidino, morpholino, etc.

The above-mentioned mono- or di-substituted amino groups or cyclic amino groups may be further substituted, and examples of such substituents may include $C_{1-4}$alkyl (e.g., methyl and ethyl), hydroxyl, $C_{1-4}$alkoxy (e.g., methoxy and ethoxy), $C_{1-4}$alkylthio (e.g., methylthio and ethylthio), carboxyl, prenyl or poly(2-10)prenyl (e.g., geranyl, farnesyl, neryl, soranesyl, geranylgeranyl, etc.), aralkyl (e.g., benzyl, 3,4,5-trimethoxybenzyl, 3,4-methylenedioxybenzyl, etc.) and the like. As specific examples of the mono- or di-substituted amino groups having such substituents, there may be mentioned 2-methoxyethylamino, 2-methylthioethylamino, carboxymethylamino, 2-hydroxyphenylamino, 4-hydroxyphenylamino, 3,4-dihydroxyphenylamino, 1-carboxy-3-methylthiopropylamino, α-carboxybenzylamino, etc., while specific examples of the cyclic amino groups having such substituents include 4-(3,4,5-trimethoxybenzyl)piperazinyl, 4-(3,4-methylenedioxybenzyl)piperazinyl, 4-(3,4-dimethoxybenzyl)piperazinyl, 4-(2-methyl-2-butenyl)piperazinyl, 4-geranylpiperazinyl, 4-farnesylpiperazinyl, 4-(3-pyridylmethyl)piperazinyl, 4-(2-furfuryl)piperazinyl, and the like.

As $R^2$ may be mentioned, by way of example, residues of compounds having amino group such as aminosaccharides (e.g., glucosamine), catecholamines (e.g., norepinephrine, epinephrine), amino acids (e.g., arginine, histidine, proline, methionine, cysteine, glutamic acid, phenylalanine, tyrosine, valine, threonine, serine, leucine, etc.), amino-containing nucleosides (e.g., adenosine, guanosine, cytidine, β-cytosine arabinoside, etc.) and the like.

With regard to the above-mentioned formula (Ib), as the protective group represented by $R^3$ may be mentioned groups normally employed for protecting the hydroxyl, such as $C_{1-3}$alkyl (e.g., methyl), $C_{1-3}$alkoxymethyl (e.g., methoxymethyl), $C_{2-4}$alkanoyl (e.g., acetyl), benzyl, tetrahydropyranyl and tetrahydrofuranyl.

A preferred embodiment provides compounds (Ia) wherein $R^2$ is (1) amino, (2) a mono- or di-substituted amino group selected from the class consisting of mono- or di-$C_{1-6}$alkylamino, $C_{3-6}$cycloalkylamino, $C_{3-6}$cycloalkyl-$C_{1-3}$alkylamino, phenyl-$C_{1-3}$alkylamino, pyridyl-$C_{1-3}$alkylamino, $C_{1-4}$alkoxyamino, anilino, hydrazino, phenylhydrazino, m-trifluoromethylphenylhydrazino, N,N-dimethylhydrazino, histamino, tryptamino, N,N'-dicyclohexylureido, 4-methyl-1-piperazinylamino and 5-(1H-tetrazolyl)amino, (3) a cyclic amino group selected from the class consisting of azetidinyl, pyrrolidinyl, piperazinyl, piperidino and morpholino, or (4) a residue of an amino-containing compound selected from the class consisting of glucosamine, norepinephrine, epinephrine, catecholamino, arginine, histidine, proline, methionine, cysteine, glutamic acid, phenylalanine, tyrosine, valine, threonine, serine, leucine, adenosine, guanosine, cytidine and β-cytosine arabinoside, said mono- or di-substituted amino and cyclic amino groups being unsubstituted or substituted by $C_{1-4}$alkyl, hydroxy, $C_{1-4}$alkoxy, $C_{1-4}$alkylthio, carboxyl, one of mono- to decaprenyl, benzyl, 3,4,5-trimethoxybenzyl or 3,4-methylenedioxybenzyl.

The compounds (Ia) and (Ib) of the present invention can be produced, for example, by reacting a carboxylic acid of the formula:

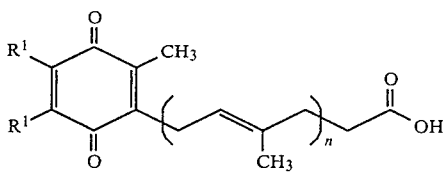

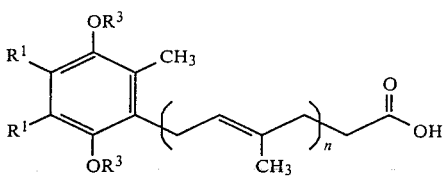

wherein n and $R^1$ are as defined above and $R^3$ is a protective group, or its reactive derivative in connection with the carboxyl function, with a compound of the formula:

$$R^2\text{—H} \qquad \text{(III)}$$

wherein $R^2$ is amino which may be substituted, to convert into an amide derivative.

The reaction between the carboxylic acid (IIa) or (IIb) and the compound (III) is normally conducted in the presence of an appropriate active condensing agent. Said condensing agent includes N,N'-dicyclohexylcarbodiimide (DCC), N-hydroxybenzotriazole and DCC, N-hydroxysuccinimide and DCC, 2-thiazoline-2-thiol and DCC, p-nitrophenol and DCC, chlorocarbonic ester and triethylamine, etc. The amount of a condensing agent suggested to be used is normally in the range of about 1 to 2 molar equivalents to (IIa) or (IIb).

The reaction is normally conducted at a reaction temperature within the range of $-20°$ C. to $150°$ C. in a suitable organic solvent (e.g., dichloromethane, tetrahydrofurane, acetonitrile, dimethylacetamide, dimethylformamide and 1,2-dimethoxyethane).

As the reactive derivative of the carboxylic acid (IIa) or (IIb) may be mentioned, by way of example, acid chlorides, mixed acid anhydrides, active esters, active amides, etc. Said agents are obtainable by methods conventional per se; for example, acid chlorides may be obtained by reacting the carboxylic acid (IIa) or (IIb) with phosphorus pentachloride, oxalic chloride, thionyl chloride, carbon tetrachloride-triphenylphosphine, phosgene, etc. The amidation reaction may be conducted under usual conditions of peptide synthesis, for example, by reacting the acid chloride (IIa) or (IIb) with (III) in the presence of an organic base (e.g., triethylamine, pyridine, etc.) or an inorganic base (e.g., sodium carbonate, potassium carbonate, etc.).

The quinone compound (Ia) and its hydroquinone form (Ib) produced in this manner can be isolated by separation and purification procedures conventional per se (e.g., chromatography and crystallization), etc. In the meanwhile, (Ia) and (Ib) are mutually convertible through a reaction conventional per se. Thus, in order to derive (Ia) from the protected hydroquinone (Ib), or inversely in order to convert (Ia) into (Ib), the intended objective can be achieved by subjecting (Ib) to a conventional reaction of removing the protective group (e.g., acidic hydrolysis, alkaline hydrolysis, etc.) and then to oxidation reaction of hydroquinone (e.g., air oxidation and ferric chloride oxidation) or by subjecting (Ib) to oxidative demethylation reaction, or by subjecting (Ia) to reduction (e.g., reduction with sodium boron hydride or sodium thiosulfate) and to a reaction of introducing a protective group (e.g., etherification, benzylation and acylation), if necessary.

The compounds (Ia) and (Ib), in cases in which the $R^2$ group contains a basic nitrogen-functional group derived from, for example, piperazine or pyridine skeleton, may form acid addition salts. Said salts include organic-acid (e.g., acetic acid, malonic acid, fumaric acid, maleic acid, succinic acid, oxalic acid, citric acid and tartaric acid) salts and inorganic-acid (e.g., hydrochloric acid, phosphoric acid, sulfuric acid and nitric acid) salts. Furthermore, the compounds (Ia) and (Ib), in cases in which the $R^2$ group contains for example a carboxyl group derived from an amino acid, may form alkali-metal (e.g., lithium, sodium and potassium) salts. Such salts are naturally included in the scope of the compounds of the present invention.

The compounds of the present invention (Ia) and (Ib) possess regulatory action for the prostaglandin biosynthesis (modulating of the prostaglandin $E_2$ and $I_2$ activities), inhibitory action of SRS-A (slow reacting substance of anaphylaxis) and a blocking effect of adrenaline-like action, and exhibit in animals, particularly in mammals (e.g., rat, mouse, guinea-pig, dog, rabbit and man) various physiological actions such as blood-pressure decreasing, analgesic, antiulcer, antiinflammatory, diuretic, immuno-regulatory, antiasthmatic, antiallergic, platelet aggregation inhibiting and cerebral-circulation improving actions. They are thus of value as drugs, such as an antihypertensive agent, analgesic, antiulcer agent, antiinflammatory agent, diuretic, immuno-regulating agent, antiasthmatic agent, antiallergic agent, antithrombotic agent and cerebral-circulation improving agent, as well as being of use for treatment, improvement and prevention of, for example, hypertension, cerebral thrombosis, ischemic myocardial infraction, coronary artery disorders, unbalance of the prostaglandin- and thromboxane-biosynthesis regulating mechanisms, immuno-defficiency, bronchial asthma and allergosis.

The compounds of the present invention are low in toxicity, and can be safely administered either orally or parenterally, directly or as pharmaceutical compositions [e.g., tablets, capsules (inclusive of soft capsules and microcapsules), solutions, injections and suppositories] formed by mixing with pharmaceutically acceptable carriers, excipients, etc. conventional per se. The dosage varies depending upon type of hosts, administration route, symptom, etc., but in the case of oral administration to human adults with hypertension or bronchial asthma, it is suitably employed in a single dose within the range of, normally about 0.2 mg/kg to 25 mg/kg of body weight, preferably about 0.5 to 10 mg/kg body weight, 1 to 3 times daily.

The compounds, which are the starting materials (IIa) and (IIb) and their esters, of the following formula:

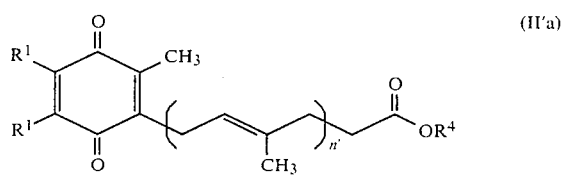

wherein n' is an integer of 2 to 10, $R^1$ is as defined above, and $R^4$ is hydrogen, $C_{1-4}$alkyl or +CH$_2$—CH=C(CH$_3$)—CH$_2$)$_{\overline{m}}$H (wherein m is an integer of 1 to 10), and their hydroquinone forms, also have the same physiological activities and utility as those of the compounds (Ia) and (Ib), and they can be used in accordance with the same manners as those of (Ia) and (Ib).

The hydroquinone forms of the above quinone compounds (II'a) are represented by the formula:

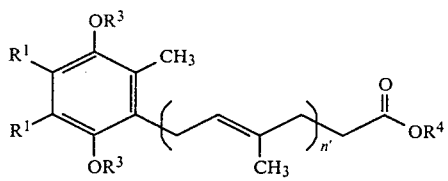

(II'b)

wherein all symbols are as defined above.

With regard to the above formulas (II'a) and (II'b), $C_{1-4}$alkyl groups represented by $R_2$ include, for example, methyl, ethyl, propyl, isopropyl, butyl, isobutyl, sec-butyl and tert-butyl.

The compounds (II'a) and (II'b) can be produced by reacting a compound of the formula:

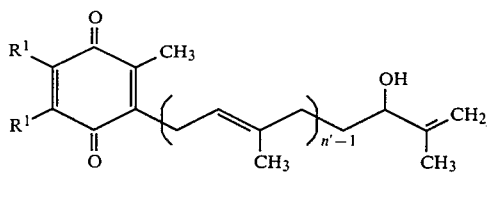

(IIIa)

or

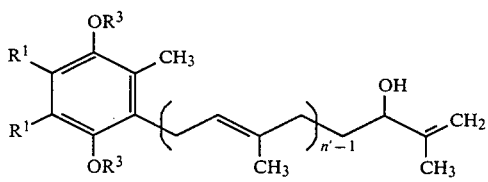

(IIIb)

wherein n', $R^1$ and $R^3$ are as defined hereinbefore, with an orthoacetate and, if necessary, subjecting the obtained ester compound to hydrolysis to produce a carboxylic acid compound and, if further necessary, subjecting the carboxylic acid compound to esterification.

As examples of the orthoacetate may be mentioned $C_{1-4}$alkyl esters of orthoacetic acid, such as trimethyl orthoacetate and triethyl orthoacetate, and the $C_{1-4}$alkyl groups in said esters correspond to the $C_{1-4}$alkyl groups as $R^4$. The reaction of (IIIa) or (IIIb) with orthoacetate is usually allowed to proceed by heating in the presence of an acid catalyst. Among preferred examples of such an acid catalyst are lower fatty acids (e.g., acetic acid and propionic acid), and the reaction temperature is normally in the range of 100° to 180° C., preferably in the range of about 130° to 150° C. Referring to a suitable solvent, the above-mentioned orthoacetate or acid catalyst can be employed as a substitute for the solvent, and toluene, xylene, dichloroethylene, etc., may be used as well.

The compounds (II'a) and (II'b) where $R^4$ is a hydrogen atom, thus the compounds (IIa) and (IIb) are obtained by hydrolyzing in the presence of a base the compounds (II'a) and (II'b) where $R^4$ is $C_{1-4}$alkyl group as produced through the above-mentioned reaction. As examples of such base may be mentioned sodium hydroxide, potassium hydroxide, etc. The compound (II'a), being unstable in alkaline conditions, is desirably hydrolyzed normally after being reduced to the hydroquinone derivative (II'b) by the use of a suitable reducing agent (e.g., sodium boron hydride, sodium hydrosulfite, etc.), and the compound (II'a) where $R^4$ is hydrogen can be produced by oxidizing the hydrolyzed (II'b) with a mild oxidizing agent (e.g., air, ferric chloride, silver oxide) in accordance with a conventional procedure.

The compounds (IIa) and (IIb) where n is 1 can be produced by a similar procedure to that mentioned above.

The compound (II'a) or (II'b) where $R^4$ is hydrogen can be converted into the compound (II'a) or (II'b) where $R^4$ is a $C_{1-4}$alkyl group or a (poly)prenyl group, —(CH$_2$—CH=C(CH$_3$)—CH$_2$)$_m$—H radical [wherein m is as defined hereinbefore] by esterifying with a lower alcohol or (poly)prenyl alcohol or their reactive derivative. As examples of the reactive derivative may be mentioned halides (e.g., chloride and bromide) of lower alcohols or (poly)prenyl alcohols. Examples of the —(CH$_2$—CH=C(CH$_3$)—CH$_2$)$_m$—H group introduced by the (poly)prenyl alcohol include prenyl, geranyl, neryl, farnesyl, tetraprenyl, pentaprenyl, hexaprenyl, heptaprenyl, octaprenyl, nonaprenyl(soranesyl) and decaprenyl. The above-mentioned esterification is allowed to proceed by treating in a polar solvent such as dimethylformamide, dimethylsulfoxide and tetrahydrofurane at room temperature or under warming (about 30° to 50° C.) by the use of a dehydrohalogenating agent such as organic amines (e.g., pyridine, triethylamine, etc.), potassium carbonate and sodium carbonate. In case in which the compound (II'b) is subjected to the esterification reaction, $R^3$ is preferably the protective group.

The produced compounds (II'a) and (II'b) are mutually convertible by a procedure conventional per se such as oxidation-reduction reaction.

The compounds (II'a) and (II'b) of the present invention produced by the above procedure can be isolated from a reaction mixture by conventional separation and purification means (e.g., chromatography, crystallization, etc.). The compounds (II'a) and (II'b) where $R^2$ is hydrogen, thus (IIa) and (IIb) may be isolated, in the usual methods, as salts such as alkali metal salts (e.g., sodium salt, potassium salt, etc.) and alkaline earth metal salts (e.g., calcium slat, magnesium salt, etc.), and such salts are also included in the scope of the compound of the present invention.

Thus, as a whole, the present invention provides the following compounds of the formula:

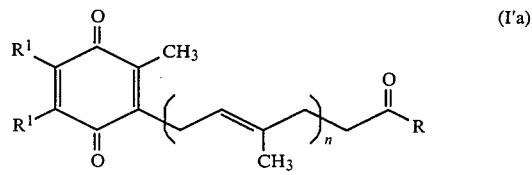

(I'a)

wherein $R^1$ is as defined hereinbefore, R is $R^2$ or —OR$^4$ (wherein $R^2$ and $R^4$ are as defined above), and is an integer of 1 to 10 when R is $R^2$ or n is an integer of 2 to 10 when R is —OR$^4$, and their hydroquinone forms.

The above-mentioned compounds (IIIa) and (IIIb) can be produced by known procedures described in literature, for example, Journal of the Chemical Society, Perkin Transactions I, pp. 1101 (1978), The Journal of Organic Chemistry, vol. 44, pp. 868 (1979) and Synthesis, pp. 574 (1979), or equivalent procedures, as described below in the equation:

tate (3 to 30 ml), and propionic acid (0.01 to 0.1 ml) was added to the solution. The reaction mixture was heated at 100° to 140° C. to distill the ethanol or methanol off as produced in the course of reaction. After 1.5 to 5 hours, the reaction solution was concentrated under

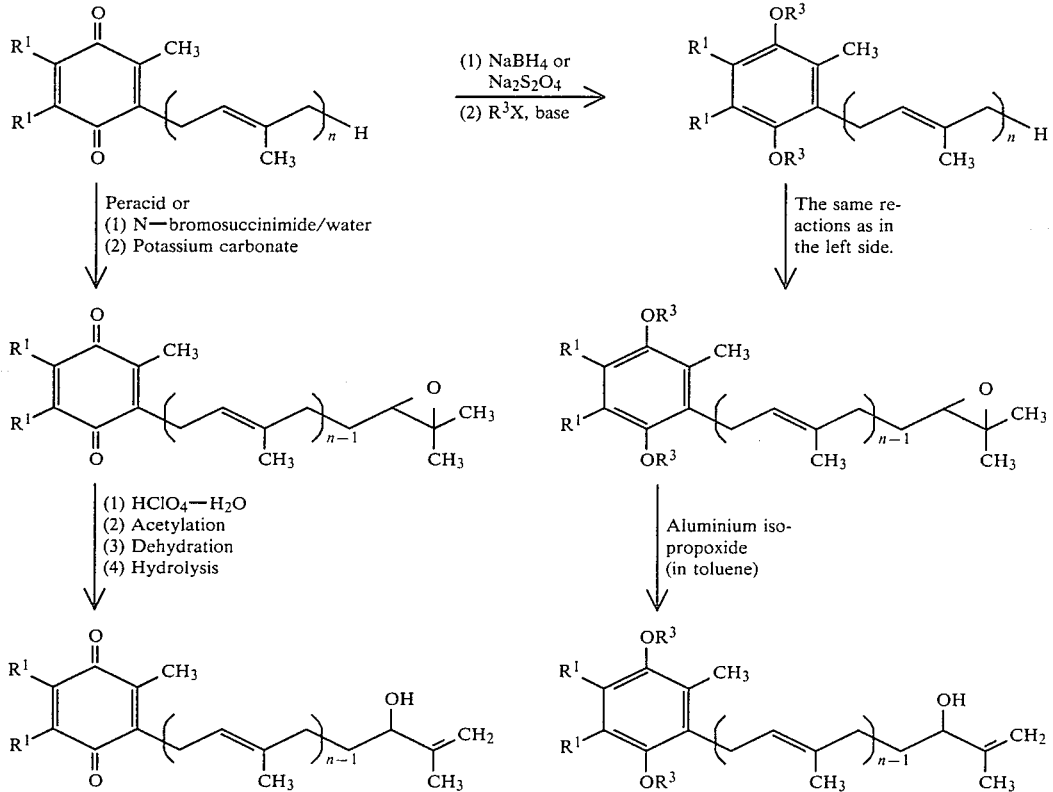

[wherein X is halogen (e.g., chlorine, bromine and iodine), and other symbols are as defined hereinbefore].

Examples are given below to illustrate the present invention in more detail, but are not intended to limit the scope of the present invention.

EXAMPLE 1

Production of quinone carboxylic acid esters (IIa-1, IIa-2) or protected hydroquinone carboxylic acid esters (IIb-1 to IIb-13)

An allyl alcohol form (IIIa or IIIb; 1 to 10 mmol) was dissolved in triethyl orthoacetate or trimethyl orthoacereduced pressure to distill off the excessive reagents, and the residue was chromatographed on silica gel (10 to 100 g). Elution with a solvent based on hexane-isopropyl ether yielded the desired hydroquinone compound (IIb-1 to IIb-13) and quinone compound (IIa-1, IIa-2). The compounds and their physical properties are shown in Table 1.

TABLE 1

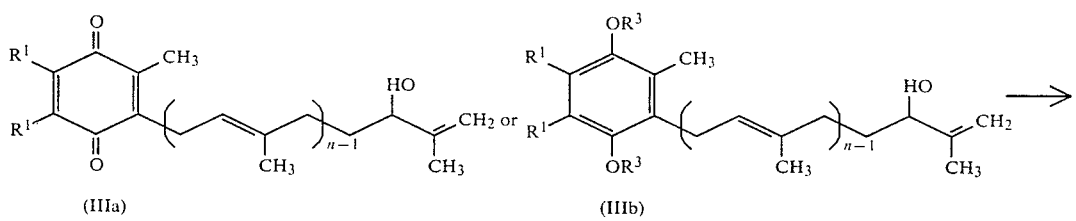

TABLE 1-continued

Structures (IIa) and (IIb):

(IIa): quinone with R¹ groups, CH₃, and side chain $-(CH_2)-CH=C(CH_3)-(...)_n-CH_2-C(=O)-OR^4$ (IIb): aromatic with OR³, R¹, CH₃, OR³, and similar side chain ending in $-OR^4$

| Starting material | Product | R¹ | R⁴ | R³ | n | Molecular formula (Molecular weight) | NMR spectrum [in CDCl₃ TMS internal standard, δ(ppm)] |
|---|---|---|---|---|---|---|---|
| IIIb-1 | IIb-1 | (cyclohexadienyl) | CH₂CH₃ | CH₃ | 2 | C₂₇H₃₆O₄ (424.56) | 1.20(3H), 1.56(3H), 1.82 (3H), 2.30(4H), 2.38(3H), 3.56(2H), 3.86(3H), 3.88 (3H), 4.08(2H), 4.96–5.23 (2H), 7.2–7.6(2H), 7.9–8.2(2H) |
| IIIb-2 | IIb-2 | (cyclohexadienyl) | CH₂CH₃ | CH₃ | 3 | C₃₂H₄₄O₄ (492.67) | 1.21(3H), 1.57(6H), 1.82 (3H), 2.29(4H), 2.38(3H), 3.56(2H), 3.86(3H), 3.88 (3H), 4.07(2H), 4.96–5.25 (3H), 7.3–7.6(2H), 8.0–8.15(2H) |
| IIIb-3 | IIb-3 | (cyclohexadienyl) | CH₂CH₃ | CH₃ | 4 | C₃₇H₅₂O₄ (620.84) | 1.20(3H), 1.58(9H), 1.82 (3H), 2.30(4H), 2.38(3H), 3.56(2H), 3.86(3H), 3.88 (3H), 4.08(2H), 4.96–5.25 (4H), 7.3–7.6(2H), 8.0–8.15(2H) |
| IIIb-4 | IIb-4 | (cyclohexadienyl) | CH₂CH₃ | CH₃ | 9 | C₆₂H₉₂O₄ (893.29) | 1.21(3H), 1.61(24H), 1.82 (3H), 2.0(CH₂), 2.30(4H), 2.38(3H), 3.56(2H), 3.86 (3H), 3.88(3H), 4.07(2H), 4.9–5.3(9H), 7.3–7.5(2H), 8.0–8.2(2H) |
| IIIb-5 | IIb-5 | CH₃ | CH₂CH₃ | CH₃ | 2 | C₂₅H₃₈O₄ (402.55) | 1.21(3H), 1.55(3H), 1.74(3H) 2.14(9H), 2.32(4H), 3.32(2H) 3.60(6H), 4.08(2H), 4.9–5.15(2H) |
| IIIb-6 | IIb-6 | CH₃ | CH₂CH₃ | CH₃ | 3 | C₃₀H₄₆O₄ (470.67) | 1.20(3H), 1.56(3H), 1.72 (3H), 2.14(9H), 2.32(4H), 3.32(2H), 3.60(6H), 4.08 (2H), 4.9–5.15(3H) |
| IIIb-7 | IIb-7 | CH₃ | CH₂CH₃ | CH₃ | 4 | C₃₅H₅₄O₄ (538.78) | 1.20(3H), 1.58(3H), 1.74 (3H), 2.14(9H), 2.32(4H), 3.32(2H), 3.60(6H), 4.08 (2H), 4.9–5.15(4H) |
| IIIb-8 | IIb-8 | OCH₃ | CH₂CH₃ | CH₂—O—CH₃ | 2 | C₂₇H₄₂O₈ (494.61) | 1.20(3H), 1.58(3H), 1.78 (3H), 2.05(CH₂), 2.20(3H), 2.34(4H), 3.46(2H), 3.58 (6H), 3.88(6H), 4.10(2H), 5.11(4H), 5.2(2H) |
| IIIb-9 | IIb-9 | OCH₃ | CH₂CH₃ | CH₂—O—CH₃ | 3 | C₃₂H₅₀O₈ (562.72) | 1.20(3H), 1.58(6H), 1.78 (3H), 2.0(CH₂), 2.20(3H), 2.34(4H), 3.46(2H), 3.58 (6H), 3.88(6H), 4.10(2H), 5.11(4H), 4.9–5.2(3H) |
| IIIb-10 | IIb-10 | OCH₃ | CH₂CH₃ | CH₂—O—CH₃ | 4 | C₃₇H₅₈O₈ (630.83) | 1.20(3H), 1.59(9H), 1.78 (3H), 2.0(CH₂), 2.20(3H), 2.34(4H), 3.46(2H), 3.58 (6H), 3.88(6H), 4.10(2H), 5.10(4H), 4.9–5.2(4H) |
| IIIb-11 | IIb-11 | OCH₃ | CH₂CH₃ | CH₂—O—CH₃ | 7 | C₅₂H₈₂O₈ (835.18) | 1.20(3H), 1.59(18H), 1.78 (3H), 2.0(CH₂), 2.20(3H), 2.34(4H), 3.46(2H), 3.58 (6H), 3.88(6H), 4.13(2H), 5.10(4H), 4.9–5.3(7H) |
| IIIb-12 | IIb-12 | OCH₃ | CH₂CH₃ | CH₂—O—CH₃ | 10 | C₆₇H₁₀₆O₈ (1049.52) | 1.20(3H), 1.61(27H), 1.78 (3H), 2.0(CH₂), 2.20(3H), 2.34(4H), 3.46(2H), 3.58 (6H), 3.88(6H), 4.10(2H), 5.10(4H), 4.9–5.3(10H) |
| IIIb-13 | IIb-13 | OCH₃ | CH₃ | CH₂—O—CH₃ | 2 | C₂₆H₄₀O₆ (448.58) | 1.57(3H), 1.78(3H), 2.05 (CH₂), 2.20(3H), 2.34(4H), |

TABLE 1-continued

| | | | | | | | |
|---|---|---|---|---|---|---|---|
| | | | | | | | 3.46(2H), 3.58(6H), 3.83 (3H), 3.88(6H), 4.10(2H), 5.11(4H) |
| IIIa-1 | IIa-1 | $OCH_3$ | $CH_2CH_3$ | — | 2 | $C_{23}H_{32}O_6$ (404.49) | 1.20(3H), 1.57(3H), 1.74 (3H), 1.98($CH_3 + CH_2$), 2.34(4H), 3.18(2H), 3.97 (3H), 3.99(3H), 4.10(2H), 4.9–5.3(2H) |
| IIIa-2 | IIa-2 | $OCH_3$ | $CH_2CH_3$ | — | 7 | $C_{48}H_{72}O_6$ (745.06) | 1.21(3H), 1.60(18H), 1.74 (3H), 2.0($CH_2$), 2.34(4H), 3.18(2H), 3.97(3H), 3.99 (3H), 4.10(2H), 4.8–5.3 (7H) |

EXAMPLE 2

(a) Production of protected hydroquinone carboxylic acids (IIb-14 to IIb-20)

A hydroquinone carboxylic acid ester (IIb-1 to 3, 5, 8 and 9; each 10 mmol) was dissolved in methanol (20 ml), to which was added a 10% aqueous solution of sodium hydroxide (3 ml) to hydrolize the ester at room temperature or while being warmed at 40° to 50° C. After the completion of the reaction, methanol was distilled off under reduced pressure, and ether (100 ml) was added, followed by acidifying the mixture with phosphoric acid. The ether layer was washed with water, dried ($Na_2SO_4$) and concentrated, thus yielding the desired, protected hydroquinone carboxylic acid (IIb-14 to IIb-20). The compounds and their physical properties are shown in Table 2.

(b) Production of protected hydroquinone carboxylic acid esters (IIb-21 to IIb-27)

A protected hydroquinone carboxylic acid (IIb-14 to IIb-20; 2 mmol) was dissolved in dimethylacetamide, and geranyl or farnesyl bromide (2.2 mmol) and potassium carbonate (2.2 mmol) were added to the solution, followed by warming at 40° to 45° C. After the completion of the reaction, isopropyl ether and water were added to the mixture and shaken. The organic layer was washed with water, dried ($Na_2SO_4$) and concentrated. The residue was chromatographed on silica gel. Elution with hexane-isopropyl ether (9:1) yielded the desired ester (IIb-21 to IIb-27). The compounds and their physical properties are shown in Table 2.

TABLE 2

(IIb)

| Product | $R^1$ | $R^4$ | $R^3$ | n | Molecular formula (Molecular weight) | NMR spectrum [in $CDCl_3$ TMS internal standard, δ(ppm)] |
|---|---|---|---|---|---|---|
| IIb-14 |  | H | $CH_3$ | 2 | $C_{25}H_{32}O_4$ (396.51) | 1.59(3H), 1.80(3H), 2.24(3H), 2.35 (4H), 3.58(2H), 3.83(6H), 4.88–5.24 (2H), 7.16–7.54(2H), 7.80–8.16(2H) |
| IIb-15 |  | H | $CH_3$ | 3 | $C_{30}H_{40}O_4$ (464.62) | 1.60(6H), 1.80(3H), 2.24(3H), 2.34 (4H), 3.58(2H), 3.84(6H), 4.8–5.25 (3H), 7.16–7.55(2H), 7.80–8.16(2H) |
| IIb-16 | 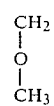 | H | $CH_3$ | 4 | $C_{35}H_{48}O_4$ (532.73) | 1.60(9H), 1.80(3H), 2.25(3H), 2.34 (4H), 3.58(2H), 3.83(6H), 4.8–5.25 (4H), 7.15–7.54(2H), 7.80–8.16(2H) |
| IIb-17 | $CH_3$ | H | $CH_3$ | 2 | $C_{23}H_{34}O_4$ (374.50) | 1.66(3H), 1.75(3H), 2.16(9H), 2.34 (4H), 3.40(2H), 3.60(6H), 4.80–5.20 (2H) |
| IIb-18 | $OCH_3$ | H | $\begin{array}{c}CH_2\\|\\O\\|\\CH_3\end{array}$ | 2 | $C_{25}H_{38}O_8$ (466.55) | 1.60(3H), 1.76(3H), 2.0–2.4(4H), 2.20(3H), 2.35(4H), 3.46(2H), 3.58 (6H), 3.88(6H), 5.10(4H), 5.2(2H) |

TABLE 2-continued

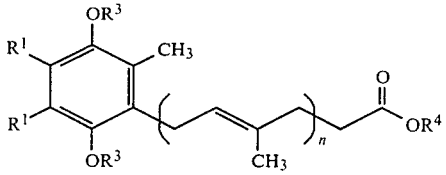

(IIb)

| Product | R¹ | R⁴ | R³ | n | Molecular formula (Molecular weight) | NMR spectrum [in CDCl₃ TMS internal standard, δ(ppm)] |
|---|---|---|---|---|---|---|
| IIb-19 | OCH₃ | H | $\mathrm{CH_2\text{-}O\text{-}CH_3}$ | 3 | $C_{30}H_{46}O_8$ (534.67) | 1.60(6H), 1.76(3H), 2.0(CH₂), 2.20 (3H), 2.35(4H), 3.46(2H), 3.58(6H), 3.88(6H), 5.0-5.2(3H), 5.10(4H) |
| IIb-20 | OCH₃ | H | $\mathrm{CH_2\text{-}O\text{-}CH_3}$ | 7 | $C_{50}H_{78}O_8$ (807.12) | 1.60(18H), 1.76(3H), 2.0(CH₂), 2.20 (3H), 2.35(4H), 3.46(2H), 3.58(6H), 3.88(6H), 4.8-5.2(6H), 5.10(4H) |
| IIb-21 | 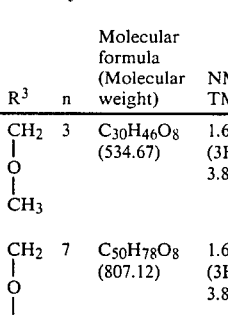 | 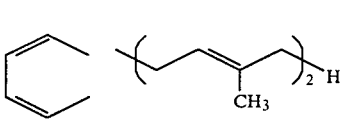 | CH₃ | 2 | $C_{35}H_{48}O_4$ (532.73) | 1.60(6H), 1.70(6H), 1.80(3H), 2.24 (3H), 2.35(4H), 3.58(2H), 3.83(6H), 4.65(2H), 4.9-5.3(4H), 7.16-7.55 (2H), 7.8-8.2(2H) |
| IIb-22 | 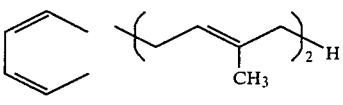 | (same as above) | CH₃ | 3 | $C_{40}H_{56}O_4$ (600.85) | 1.60(9H), 1.70(6H), 1.80(3H), 2.24 (3H), 2.35(4H), 3.58(2H), 3.83(6H), 4.65(2H), 4.9-5.3(5H), 7.16-7.55 (2H), 7.8-8.2(2H) |
| IIb-23 | 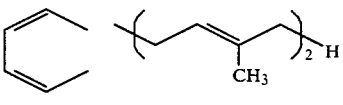 | (same as above) | CH₃ | 4 | $C_{45}H_{64}O_4$ (668.96) | 1.60(12H), 1.70(6H), 1.80(3H), 2.0 (CH₂), 2.24(3H), 2.35(4H), 3.58(2H), 3.83(6H), 4.65(2H), 4.8-5.3(6H), 7.16-7.55(2H), 7.8-8.2(2H) |
| IIb-24 | CH₃ | 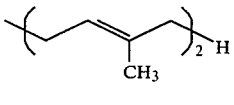 | CH₃ | 2 | $C_{33}H_{50}O_4$ (510.73) | 1.60(3H), 1.70(6H), 1.75(3H), 2.16 (9H), 2.34(4H), 3.60(6H), 4.65(2H), 4.8-5.3(4H) |
| IIb-25 | OCH₃ | 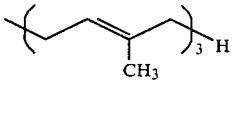 | $\mathrm{CH_2\text{-}O\text{-}CH_3}$ | 2 | $C_{40}H_{62}O_8$ (670.90) | 1.60(9H), 1.75(9H), 2.0(CH₂), 2.20 (3H), 2.35(4H), 3.46(2H), 3.58(6H), 3.88(6H), 4.65(2H), 5.10(4H), 5.0-5.3(5H) |
| IIb-26 | OCH₃ | 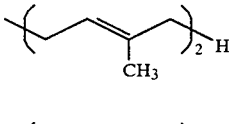 | $\mathrm{CH_2\text{-}O\text{-}CH_3}$ | 3 | $C_{40}H_{62}O_8$ (670.90) | 1.60(9H), 1.76(9H), 2.0(CH₂), 2.20 (3H), 2.35(4H), 3.46(2H), 3.58(6H), 3.88(6H), 4.65(2H), 5.10(4H), 5.0-5.3(5H) |
| IIb-27 | OCH₃ | 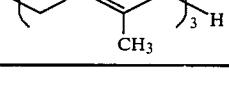 | $\mathrm{CH_2\text{-}O\text{-}CH_3}$ | 7 | $C_{65}H_{102}O_8$ (1011.46) | 1.60(24H), 1.76(9H), 2.0(CH₂), 2.35 (4H), 3.46(2H), 3.58(6H), 3.88(6H), 4.65(2H), 5.10(4H), 4.8-5.3(10H) |

EXAMPLE 3

Production of quinone carboxylic acids or their salts (IIa-3 to IIb-15)

Method A:

A protected hydroquinone carboxylic acid (IIb-1 to IIb-7)(5 to 10 mmol) was dissolved in tetrahydrofuran (20 to 40 ml) and a 2N aqueous solution of sodium hydroxide (3 to 6 ml) was added to the solution, followed by warming for 4 to 10 hours to conduct hydrolysis. After the completion of the reaction, tetrahydrofuran was removed under reduced pressure, and the solution was acidified with aqueous phosphoric acid. The resulting carboxylic acid is extracted with ethyl acetate. The organic layer was washed with water, dried and concentrated. The residue (4 to 5 mmol) was dissolved in dioxane-ether (2:1) (40 to 60 ml), and silver oxide (AgO) (6 to 10 mmol) was added, followed by adding gradually a 0.5N aqueous solution of nitric acid (12 to 20 ml) to the mixture under stirring. For 20 minutes after dropwise adding the aqueous nitric acid solution, the reaction was allowed to proceed in the same conditions, and water (100 ml) was added to the solution. The product was extracted with ether. The ether layer was washed with water, dried (Na₂SO₄), and concentrated under a reduced pressure. The residue was chromatographed on silica gel inactivated by water, and elution with ether-isopropyl ether yielded the desired quinone carboxylic acid (IIa-3 to IIa-9). The compounds and their physical properties are shown in Table 3.

Method B:

A protected hydroquinone carboxylic acid ester (IIb-8 to IIb-13) (5 mmol) was dissolved in methanol (50 ml), and a 2N aqueous solution of sodium hydroxide (7 ml) was added to the solution to hydrolize of the ester for 3 to 4 hours. After the completion of the reaction, the reaction mixture was cooled and methanol was removed under reduced pressure, and the residue was then acidified with phosphoric acid to extract the resulting carboxylic acid with ethyl acetate. The organic layer was washed with water, dried (Na₂SO₄) and concentrated. The residue was dissolved in acetone (50 ml), and a 2N aqueous sulfuric acid (3 ml) was added, followed by warming at 40° to 50° C. for 4 to 6 hours. After the completion of the hydrolysis, the reaction solution was cooled, and a 16% aqueous solution of ferric chloride (2 ml) was added to oxidize the hydroquinone at room temperature for 30 minutes. The reaction solution was added with water (100 ml) to extract the product compound with ether. The organic layer was washed with water, dried (Na₂SO₄) and concentrated. The residue was chromatographed on silica gel, and elution with a solvent based on isopropyl ether-ether yielded the desired quinone carboxylic acid (IIa-10, IIa-12 to IIa-15). The compounds and their physical properties are shown in Table 3.

Method C:

A quinone carboxylic acid ester (IIa-1, IIa-2) (2 mmol) was dissolved in methanol (20 ml), and reduced with sodium boron hydride (100 mg) under a nitrogen stream. After the reaction solution became colorless, a 2N aqueous solution of sodium hydroxide (2 ml) was added and the reaction was carried out at room temperature for 5 hours. After the completion of the hydrolysis, phosphoric acid was added to acidify the solution, and a 16% aqueous solution of ferric chloride (1.0 ml) was added to oxidize the resulting hydroquinone carboxylic acid at room temperature. After 30 minutes, water was added to the reaction solution to extract the reaction product with ether. The organic layer was washed with water, dried and concentrated. The residue was chromatographed on silica gel, and elution with ether-isopropyl ether yielded the desired quinone carboxylic acid (IIa-10, IIa-14). The compounds and their physical properties are shown in Table 3.

Production of a sodium sat (IIa-11):

A quinone carboxylic acid (IIa-10) (mp. 57° C., 752 mg, 2 mmol) was dissolved in acetone (20 ml), to which sodium hydrogencarbonate (168 mg) was added. After it was completely dissolved, acetone was removed to dryness under a reduced pressure, yielding the desired sodium salt of the quinone carboxylic acid (IIa-11). The compound and its physical properties are shown in Table 3.

TABLE 3

(IIa)

| Starting material | Product | Method | R¹ | R⁴ | n | Molecular formula (Molecular weight) | NMR spectrum [in CDCl₃ TMS internal standard, δ(ppm)] |
|---|---|---|---|---|---|---|---|
| IIb-1 | IIa-3 | A |  | H | 2 | C₂₃H₂₆O₄ (366.44) | 1.57(3H), 1.89(3H), 2.0(CH₂), 2.20(3H), 2.34(4H), 3.37(2H), 4.9–5.3(2H), 7.6–7.75(2H), 8.0–8.15(2H), 9.72(1H) |
| IIb-2 | IIa-4 | A |  | H | 3 | C₂₈H₃₄O₄ (434.55) | 1.58(6H), 1.89(3H), 2.0(CH₂), 2.20(3H), 2.34(4H), 3.37(2H), 4.9–5.3(3H), 7.6–7.75(2H), 8.0–8.15(2H), 10.86(1H) |
| IIb-3 | IIa-5 | A |  | H | 4 | C₃₃H₄₂O₄ (502.67) | 1.59(9H), 1.89(3H), 2.0(CH₂), 2.20(3H), 2.34(4H), 3.37(2H), 4.9–5.3(4H), 7.6–7.75(2H), 8.0–8.15(2H), 10.22(1H) |
| IIb-4 | IIa-6 | A |  | H | 9 | C₅₈H₈₂O₄ (843.24) | 1.61(24H), 1.89(3H), 2.0(CH₂), 2.30(3H), 2.34(4H), 3.37(2H), 4.9–5.3(9H), 7.6–7.75(2H), 8.0–8.15(2H), 10.56(1H) |
| IIb-5 | IIa-7 | A | CH₃ | H | 2 | C₂₁H₂₈O₄ (344.44) | 1.60(3H), 1.76(3H), 2.01(9H), 2.34(4H), 3.24(2H), 5.2(2H), 10.23(1H) |
| IIb-6 | IIa-8 | A | CH₃ | H | 3 | C₂₆H₃₆O₄ (412.55) | 1.60(3H), 1.76(3H), 2.0(9H), 2.34(4H), 3.24(2H), 5.2(3H), |

TABLE 3-continued (IIa) structure: quinone with R¹ groups, CH₃, and side chain $(CH_2CH=C(CH_3)CH_2)_n$-CH₂-C(=O)-OR⁴

| Starting material | Product | Method | R¹ | R⁴ | n | Molecular formula (Molecular weight) | NMR spectrum [in CDCl₃ TMS internal standard, δ(ppm)] |
|---|---|---|---|---|---|---|---|
| IIb-7 | IIa-9 | A | CH₃ | H | 4 | $C_{31}H_{44}O_4$ (480.66) | 10.3(1H) 1.61(9H), 1.76(3H), 2.0(9H), 2.34(4H), 3.24(2H), 5.2(4H), 9.96(1H) |
| IIa-1 IIb-8 | IIa-10 | C B | OCH₃ | H | 2 | $C_{21}H_{28}O_6$ (376.44) | 1.60(3H), 1.75(3H), 1.98(3H + CH₂), 3.24(4H), 3.20(2H), 3.97 & 3.99 (6H), 4.8–5.3(2H), 10.83(1H) |
| IIa-10 | IIa-11 | — | OCH₃ | Na | 2 | $C_{21}H_{27}O_6Na$ (398.42) | (in CD₃OD); 1.59(3H), 1.74(3H), 1.98(3H + CH₂), 2.25(4H), 3.17(2H), 3.94(6H), 4.8–5.2(2H) |
| IIb-9 | IIa-12 | B | OCH₃ | H | 3 | $C_{26}H_{36}O_6$ (444.55) | 1.60(6H), 175(3H), 2.0(CH₃ + CH₂), 2.34(4H), 3.18(2H), 3.97 & 3.99(6H), 4.8–5.3(3H), 10.52(1H) |
| IIb-10 | IIa-13 | B | OCH₃ | H | 4 | $C_{31}H_{44}O_6$ (512.66) | 1.61(9H), 1.75(3H), 2.0(CH₃ + CH₂), 2.34(4H), 3.18(2H), 3.97 & 3.99(6H), 4.9–5.3(4H), 10.36(1H) |
| IIa-2 IIb-11 | IIa-14 | C B | OCH₃ | H | 7 | $C_{46}H_{68}O_6$ (717.00) | 1.61(18H), 1.76(3H), 2.0(CH₂), 2.34(4H), 3.18(2H), 3.97 & 3.99(6H), 4.9–5.3(6H), 10.22(1H) |
| IIb-12 | IIa-15 | B | OCH₃ | H | 10 | $C_{61}H_{92}O_6$ (921.35) | 1.61(27H), 1.76(3H), 2.0(CH₂), 2.34(4H), 3.18(2H), 3.97 & 3.99(6H), 4.9–5.3(6H), 9.92(1H) |

EXAMPLE 4

A quinone carboxylic acid (IIa-10, IIa-12, IIa-3, IIa-4, IIa-7, IIa-8) (2 mmol) was dissolved in dimethylformamide (10 ml) and potassium carbonate was added (336 mg, 2.4 mmol). To the solution was added a corresponding polyprenyl bromide (m=2, geranyl bromide; m=3, farnesyl bromide; m=9, soranesyl bromide) (2.4 mmol) at room temperature. After 6 hours, water (50 ml) was added to the reaction mixture and the product was extracted with ether. The organic layer was washed with water, dried (Na₂SO₄) and concentrated. The residue was chromatographed on silica gel, and elution with isopropyl ether yielded the desired polyprenyl ester of the quinone carboxylic acid (IIa-16 to IIa-25). The compounds and their physical properties are shown in Table 4.

TABLE 4

(IIa) structure with polyprenyl ester

| Product | R¹ | m | n | Molecular formula (molecular weight) | NMR spectrum [in CDCl₃ TMS internal standard, δ(ppm)] |
|---|---|---|---|---|---|
| IIa-16 | OCH₃ | 3 | 2 | $C_{36}H_{52}O_6$ 580.77 | 1.60(9H), 1.70(6H), 1.76(3H), 2.0(CH₂ + CH₃), 2.34(4H), 3.18(2H), 3.98 & 3.99(6H), 4.66(2H), 4.9–5.6(5H) |
| IIa-17 | OCH₃ | 3 | 3 | $C_{41}H_{60}O_6$ 648.89 | 1.60(12H), 1.70(9H), 2.0(CH₂ + CH₃), 2.34(4H), 3.18(2H), 3.97 & 3.99(6H), 4.66(2H), 4.9–5.6(6H) |
| IIa-18 | OCH₃ | 9 | 2 | $C_{66}H_{100}O_6$ 989.46 | 1.60(30H), 1.70(6H), 1.76(3H), 2.0(CH₂ + CH₃), 2.34(4H), 3.18(2H), 3.97 & 3.99(6H), 4.66(2H), 4.9–5.6(11H) |
| IIa-19 | OCH₃ | 2 | 2 | $C_{31}H_{44}O_6$ 512.66 | 1.60(6H), 1.70(6H), 1.75(3H), 2.0(CH₂ + CH₃), 2.34(4H), 3.18(2H), 3.97 & 3.99(6H), 4.66(2H), 4.9–5.6(4H) |

TABLE 4-continued

(IIa)

| Product | R¹ | m | n | Molecular formula (molecular weight) | NMR spectrum [in CDCl₃ TMS internal standard, δ(ppm)] |
|---|---|---|---|---|---|
| IIa-20 | (phenyl) | 2 | 2 | $C_{33}H_{42}O_4$ 502.67 | 1.58(6H), 1.70(6H), 1.90(3H), 2.0(CH₂), 2.20 (3H), 2.34(4H), 3.37(2H), 4.67(2H), 4.9–5.6 (4H), 7.6–7.75(2H), 8.0–8.15(2H) |
| IIa-21 | (phenyl) | 3 | 2 | $C_{38}H_{50}O_4$ 570.78 | 1.60(9H), 1.70(6H), 1.90(3H), 2.0(CH₂), 2.20 (3H), 2.34(4H), 3.37(2H), 4.67(2H), 4.9–5.6 (5H), 7.6–7.75(2H), 8.0–8.15(2H) |
| IIa-22 | (phenyl) | 3 | 3 | $C_{43}H_{58}O_4$ 638.89 | 1.60(12H), 1.70(6H), 1.90(3H), 2.0(CH₂), 2.20 (3H), 2.34(4H), 3.37(2H), 4.67(2H), 4.9–5.6 (6H), 7.6–7.75(2H), 8.0–8.15(2H) |
| IIa-23 | (phenyl) | 9 | 2 | $C_{68}H_{98}O_4$ 979.46 | 1.60(30H), 1.70(6H), 1.90(3H), 2.0(CH₂), 2.20 (3H), 2.34(4H), 3.37(2H), 4.66(2H), 4.9–5.6 (11H), 7.6–7.75(2H), 8.0–8.15(2H) |
| IIa-24 | CH₃ | 2 | 2 | $C_{31}H_{44}O_4$ 480.66 | 1.60(6H), 1.70(6H), 1.76(3H), 2.0(9H), 2.34 (4H), 3.24(2H), 4.67(2H), 4.9–5.6(4H) |
| IIa-25 | CH₃ | 3 | 3 | $C_{41}H_{60}O_4$ 616.89 | 1.60(12H), 1.70(6H), 1.76(3H), 2.0(9H), 2.34 (4H), 3.24(2H), 4.66(2H), 4.9–5.6(6H) |

EXAMPLE 5

Production of quinone compounds (Ia-1 to Ia-47) and hydroquinone compounds (Ib-1 to Ib-4)

Method A: Amidation with the use of N,N'-dicyclohexylcarbodiimide (DCC) and N-hydroxysuccinimide A carboxylic acid (IIa or IIb; 1 to 10 mmol) was dissolved in methylene chloride (5 to 50 ml), and hydroxysuccinimide (1 to 10 mmol × 1.1) was added under cooling with ice. To the solution under stirring was added N,N'-dicyclohexylcarbodiimide (DCC, 1 to 10 mmol × 1.1) to conduct the reaction at 0° C. for 15 minutes and further at room temperature for 2 hours, followed by adding an amino compound (III, 1 to 10 mmol × 1.1) to the mixture. The reaction was conducted for 1 to 3 hours under the same conditions. After the completion of the reaction, N,N'-dicyclohexyl urea was filtered off, and the filtrate was washed with water and dried (magnesium sulfate). After removal of the solvent, the residue was chromatographed on silica gel. Elution with the use of a mixed solvent based on isopropyl ether:ethyl acetate yielded the desired quinone compound (Ia) or hydroquinone compound (Ib).

Method B: Amidation with the use of 1-hydrobenzotriazole and DCC.

A carboxylic acid (IIa; 1 to 10 mmol) and 1-hydroxybenzotriazole (1 to 10 mmol × 1.1) were dissolved in methylene chloride (5 to 50 ml) under stirring and the mixture was allowed to react under ice-cooling. To the solution was added DCC (1 to 10 mmol × 1.1), followed by adding an amino compound (III, 1 to 10 mmol × 1.1). The reaction was carried out under ice-cooling for 1 hour, and then at room temperature for 1 to 3 hours. The precipitated crystals were filtered off, and the filtrate was washed with water, dried (magnesium sulfate) and concentrated. The residue was chromatographed on silica gel, and elution with a mixed solvent based on isopropyl ether-ethyl acetate, followed by collecting the desired fractions to concentrate, gave in the desired quinone compound (Ia).

Method C: Amidation with the use of 2-thiazoline-2-thiol and DCC

A carboxylic acid (IIa; 1 to 10 mmol) was dissolved in methylene chloride (5 to 50 ml), and 2-thiazoline-2-thiol (1 to 10 mmol × 1.1) and DCC (1 to 10 mmol × 1.1) were added to the solution. The mixture was allowed to react at room temperature for 20 to 30 minutes. An amino compound (III, 1 to 10 mmol × 1.1) was added to the mixture under stirring. After 1 to 3 hours, the precipitated crystals were filtered off, and the filtrate was washed with water, dried (magnesium sulfate) and concentrated. The residue was chromatographed on silica gel, and elution with a mixed solvent based on isopropyl ether:ethyl acetate, followed by collecting the desired fractions to concentrate, yielded the desired quinone compound (Ia).

Method D: Amidation with the use of N-hydroxy-5-norbornene-2,3-dicarboxyimide (HONB) and DCC A carboxylic acid (IIa; 1 to 10 mml) and HONB (1 to 10 mmol × 1.1) were dissolved in dimethylformamide (DMF, 5 to 50 ml) under stirring and cooling with ice-water. DCC was added to the stirred solution and the mixture was allowed to react for 10 minutes, and the reaction was continued at room temperature for 5 hours after removing the ice bath. A solution of cytosine arabinoside (DMF:water=4:1, 5 to 50 ml) was added to the mixture. The reaction was carried out at 80° C. for 5 hours. After the completion of the reaction, the solvent was distilled off under reduced pressure, and ethyl acetate was added to the residue. Insolubles were filtered off, and the filtrate was concentrated. The residue was chromatographed on silica gel, and elution with a solvent based on ethyl acetate:methanol, followed by collecting fractions containing the desired compound to evaporate to dryness under reduced pressure, yielded the desired compound (Ia).

Method E: Amidation via acid chloride

A carboxylic acid (IIa or IIb; 1 to 10 mmol) and triphenylphosphine (1 to 10 mmol × 1.1) were dissolved in carbon tetrachloride (5 to 50 ml), and the solution was warmed at 30° to 40° C. After the completion of the reaction, the reaction solution was cooled with ice so as to add gradually a methylene chloride solution containing an amino compound (III, 1 to 10 mmol × 1.1) and a base (e.g., pyridine, 1 to 10 mmol × 1.1). After the addition, the solution was restored to the room temperature to conduct the reaction for 10 to 20 minutes. The reaction solution was washed with water, dried (magnesium sulfate) and concentrated. The residue was chromatographed over silica gel, and developing with a solvent based on isopropyl ether:ethyl acetate, followed by concentrating the desired fractions, gave the desired quinone compound (Ia) or hydroquinone compound (Ib).

Method F: Elimination of methoxymethyl and oxidation of a hydroquinone form

A hydroquinone compound (Ib, $R^1$=CH$_3$O, $R^2$=—NHCH—(CH$_3$)$_2$, $R^3$=—CH$_2$OCH$_3$, n=2, 2.54 g, 5.0 mmol) was dissolved in 1,2-dimethoxyethane (DME, 30 ml), and 2N sulfuric acid (5.0 ml) was added to the solution, followed by stirring at 70° C. for 1 hour. After cooling, 1M ferric chloride (10 ml) was added to the reaction mixture at room temperature. After 30 minutes, DME was distilled off under reduced pressure, and to the residue were added ethyl acetate (50 ml) and water (10 ml) for extraction. The ethyl acetate layer was washed with water, dried (magnesium sulfate) and concentrated. The residue was recrystallized from isopropyl ether, resulting in the desired quinone compound ([Ia, $R^1$=OCH$_3$, $R^2$=NHCH(CH$_3$)$_2$, n=2, 1.5 g], m.p. 88° to 89° C.

Method G: Production of quinone compounds through oxidative demethylation reaction.

A hydroquinone compound (Ib, $R^1 =$ 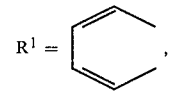, $R^2$=NH$_2$, $R^3$=CH$_3$, n=3, 4.6 g, 10 mmol) was dissolved in dioxane (56 ml), and silver oxide (AgO, 4.96 g, 40 mmol) was added to the solution, followed by adding 6N nitric acid (20 ml) with stirring at room temperature. After 30 minutes, water (150 ml) was added, and the reaction product was extracted with ethyl acetate. The organic layer was washed with water, dried (magnesium sulfate) and concentrated. The residue was chromatographed on silica gel, and elution with ethyl acetate, followed by concentration and crystallization from ethyl acetate, yielded the desired quinone compound (Ia, $R^1 =$ 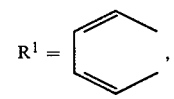, $R^2$=NH$_2$, n=3, 3.35 g), m.p. 90° to 91° C.

The compounds produced by the methods A through G as described above and their physical properties are shown in Tables givn below.

TABLE 4-A

| Product Ia- | Method | n | $R^2$ | Molecular formula (Molecular weight) |
|---|---|---|---|---|
| 1 | A | 1 | —N(piperazine)N—CH$_2$—C$_6$H$_3$—O—CH$_2$—O (methylenedioxyphenyl) | C$_{28}$H$_{34}$N$_2$O$_7$ (510.59) |
| 2 | A | 1 | —N(piperazine)N—CH$_2$—C$_6$H$_2$(OCH$_3$)$_3$ | C$_{30}$H$_{40}$N$_2$O$_8$ (556.66) |
| 3 | A | 1 | —N(piperazine)N—(CH$_2$CH=C(CH$_3$)CH$_2$)$_3$H | C$_{35}$H$_{52}$N$_2$O$_5$ (580.82) |

TABLE 4-A-continued

| Product Ia- | Method | n | R² | Molecular formula (Molecular weight) |
|---|---|---|---|---|
| 4 | A | 1 | −N⟨ ⟩ (piperidine) | $C_{20}H_{27}NO_5$ (361.44) |
| 5 | A | 1 | −NHCH₃ | $C_{17}H_{28}NO_5$ (326.42) |
| 6 | A | 2 | −N(piperazine)N−CH₂−(3,4,5-trimethoxyphenyl) | $C_{35}H_{48}N_2O_8$ (624.78) |
| 7 | A | 2 | −NH₂ | $C_{21}H_{29}NO_5$ (375.47) |
| 8 | A, F | 2 | −NHCH(CH₃)₂ | $C_{24}H_{35}NO_5$ (417.55) |
| 9 | A | 2 | −N(morpholine)O | $C_{25}H_{35}NO_6$ (445.56) |
| 10 | A | 2 | −NHCH₂COOH | $C_{23}H_{31}NO_7$ (433.51) |
| 11 | A | 3 | −N(piperazine)N−CH₂−(3,4-methylenedioxyphenyl) | $C_{38}H_{50}N_2O_7$ (646.83) |
| 12 | A | 3 | −N(piperazine)N−CH₂−(3,4,5-trimethoxyphenyl) | $C_{40}H_{56}N_2O_8$ (692.90) |
| 13 | E, D | 3 | −NH−C(=N-tetrazole) | $C_{27}H_{37}N_5O_5$ (511.61) |
| 14 | A | 3 | −NHOCH₃ | $C_{27}H_{39}NO_6$ (473.59) |
| 15 | A | 4 | −N(piperazine)N−CH₂−(3,4-methylenedioxyphenyl) | $C_{43}H_{58}N_2O_7$ (714.95) |

TABLE 4-A-continued
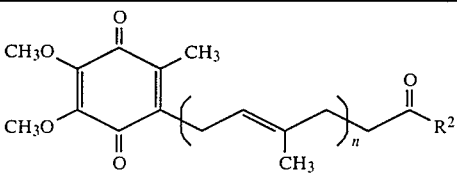
| Product Ia- | Method | n | R² | Molecular formula (Molecular weight) |
|---|---|---|---|---|
| 16 | A | 4 | 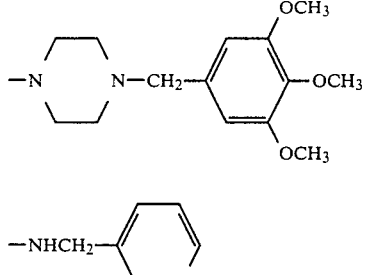 | $C_{45}H_{64}N_2O_8$ (761.02) |
| 17 | A | 7 | 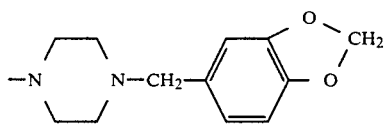 | $C_{52}H_{74}N_2O_5$ (807.18) |
| 18 | A | 7 | 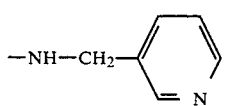 | $C_{58}H_{82}N_2O_7$ (919.31) |
| 19 | A | 7 | $-NH_2$ | $C_{46}H_{67}NO_5$ (714.05) |
| 20 | A | 10 | 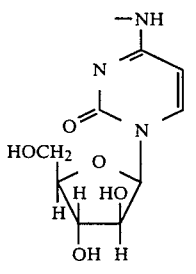 | $C_{72}H_{98}N_2O_5$ (1071.59) |
| 21 | A | 10 | $-NH_2$ | $C_{66}H_{93}NO_5$ (980.48) |
| 22 | D | 3 | 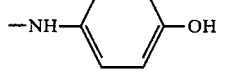 | $C_{35}H_{47}N_3O_{10}$ (669.78) |
| 22' | A | 2 | —NH—⟨C₆H₄⟩—OH | $C_{27}H_{33}O_6N$ (467.54) |
TABLE 4-B
| Product Ia- | Melting point or NMR spectrum (in CDCl3, TMS internal standard); δ(ppm) |
|---|---|
| 1 | 1.75(3H, 2.00(3H), 2.31(4H), 2.36(4H), 3.16(2H), 3,39(2H), 3.4–3.7(4H), 3.97(6H), 4.96(1H), 5.90 (2H), 6,70(2H), 6,81(1H) |
| 2 | 1.76(3H), 2.00(3H), 2.33(4H), 2.39(4H), 3.16(2H), 3.41(2H), 3.4–3.7(4H), 3.83(9H), 3.96(6H), 4.96 (1H), 6.53(2H) |
| 3 | 1.58(6H), 1.61(3H), 1.66(3H), 1.76(3H), 1.9–2.1 (8H), 2.00(3H), 2.33(4H), 2.39(4H), 2.95(2H), 3.16(2H), 3.4–3.6(4H), 3.97(6H), 4.9–5.2(4H) |
| 4 | 1.75(3H), 2.00(3H), 2.1–2.3(4H), 2.32(4H), 3.16 (2H), 3.2–3.6(4H), 3.97(6H), 4.96(1H) |
| 5 | 1.75(3H), 2.00(3H), 2.30(4H), 2.76(3H), 3.16(2H), 3.97(6H), 4.96(1H) |
| 6 | 1.59(3H), 1.71(3H), 1.9–2.1(4H), 2.00(3H), 2.36 (4H), 2.4–2.6(2H), 3.22(2H), 3.50(2H), 3.5–3.8 (2H), 3.88(3H), 3.90(6H), 4.00(6H), 4.85–5.3 (2H), 6.67(2H), |
| 7 | 59–60° C. |
| 8 | 88–89° C. |
| 9 | 1.60(3H), 1.70(3H), 1.98($CH_2$ + $CH_3$), 2.28(4H), 320(2H), 3.60(8H), 3.98(6H), 4.8–5.3(2H) |
| 10 | 1.58(3H), 1.71(3H), 1.9–2.1(4H), 2.00(3H), 2.28 |

TABLE 4-B-continued

| Product Ia- | Melting point or NMR spectrum (in CDCl3, TMS internal standard); δ(ppm) |
|---|---|
|  | (4H), 3.16(2H), 3.87(2H), 3.97(6H), 4.90(1H), 5.07(1H), 5.41(1H) |
| 11 | 1.56(3H), 1.59(3H), 1.72(3H), 1.92–2.1(8H), 2.00(3H), 2.31(4H), 2.37(4H), 3.16(2H), 3.39(2H), 3.4–3.7(4H), 3.96(6H), 4.9–5.2(3H), 5.90(2H), 6.70(2H), 6.81(1H) |
| 12 | 1.56(3H), 1.60(3H), 1.73(3H), 1.9–2.1(8H), 2.00(3H), 2.34(4H),2.41(4H), 3.16(2H), 3.42(2H), 3.4–3.7(4H), 3.83(9H), 3.96(6H), 4.9–5.2(3H), 6.53(2H) |
| 13 | 1.56(3H), 1.59(3H), 1.72(3H), 1.9–2.1(8H), 2.00(3H), 2.34(4H), 3.16(2H), 3.96(6H), 4.9–5.2(3H) |
| 14 | 1.56(3H), 1.59(3H), 1.72(3H), 1.9–2.1(8H), 2.00(3H), 2.34(4H), 3.16(2H), 3.62(3H), 3.96(6H), 4.9–5.2(3H) |
| 15 | 1.59(9H), 1.72(3H), 1.9–2.1(15H), 2.31(4H), 2.37(4H), 3.16(2H), 3.39(2H), 3.4–3.7(4H), 3.96 (6H), 4.9–5.2(4H), 5.90(2H), 6.70(2H), 6.81(1H) |
| 16 | 1.59(9H), 1.72(3H), 1.9–2.1(15H), 2.34(4H), 2.41(4H), 3.16(2H), 3.42(2H), 3.4–3.7(4H), 3.83(9H), 3.96(6H), 4.9–5.2(3H), 6.53(2H) |
| 17 | 56–58° C. |
| 18 | 1.58(1H), 1.72(3H), 1.99(27H), 2.32(4H), 2.37(4H), 3.16(2H), 3.39(2H), 3.4–3.7(4H), 3.96(6H), 4.9–5.2(7H), 5.90(2H), 6.70(2H), 6.80(1H) |
| 19 | 48–50° C. |
| 20 | 68–70° C. |
| 21 | 1.58(27H), 1.72(3H), 2.0(CH2), 2.30(4H), 3.16(2H), 3.96(6H), 4.9–5.2(10H), 5.76(2H) |
| 22 | 1.55(3H), 1.72(3H), 1.99(3H), 1.9–2.1(8H), 2.32(4H), 3.15(2H), 3.85(2H), 3.96(6H), 4.04(1H), 4.27(1H), 4.47(1H), 4.7–5.4(6H), 6.08(1H), 7.43(1H), 8.16(1H), 9.48(1H) |
| 22' | 83–86° C. |

TABLE 5-A

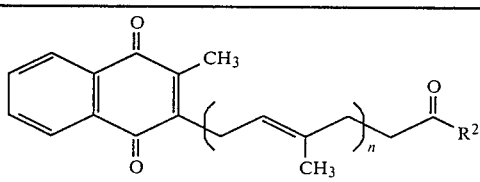

| Product Ia- | Method | n | R² | Molecular formula (Molecular weight) |
|---|---|---|---|---|
| 23 | A | 2 | —NHCH2-(3-pyridyl) | C29H32O3N2 (456.58) |
| 24 | A | 2 | —NHCHCH2CH2SCH3 \| COOH | C28H35O5NS (497.65) |
| 25 | A | 2 | —NH—N(piperazinyl)N—CH3 | C28H37O3N3·2HCl (546.65) |
| 26 | A | 2 | —NHCH(CH3)—C6H5  [L-(−)-] | C31H35O3N (469.62) |
| 27 | A | 3 | —N(piperazinyl)N—CH2-(3,4-methylenedioxyphenyl) | C40H38O5N2 (626.75) |
| 28 | A | 3 | —N(piperazinyl)N—CH2-(3,4,5-trimethoxyphenyl) | C42H54O6N2 (682.90) |
| 29 | A | 3 | —N(piperazinyl)N—CH2-farnesyl | C47H66O3N2 (707.06) |
| 30 | A, G | 3 | —NH2 | C28H35O3N (433.60) |

TABLE 5-A-continued

Structure: 2-methyl-3-[(CH₂)-CH=C(CH₃)-(CH₂)ₙ-C(=O)-R²]-1,4-naphthoquinone

| Product Ia- | Method | n | R² | Molecular formula (Molecular weight) |
|---|---|---|---|---|
| 31 | A | 3 | —N(piperidinyl) | C₃₃H₄₃NO₃ (501.68) |
| 32 | A | 3 | —N(morpholinyl) | C₃₂H₄₁NO₄ (503.66) |
| 33 | A, C | 3 | —NHCH₂CH(OH)—C₆H₃(OH)₂ | C₃₆H₄₃NO₆ (585.71) |
| 34 | A, C | 3 | —N(CH₃)CH₂CH(OH)—C₆H₃(OH)₂ | C₃₇H₄₅NO₆ (599.74) |
| 35 | A | 4 | —NHCH₂—(3-pyridyl) | C₃₉H₄₈N₂O₃ (592.83) |
| 36 | A | 4 | —NHCH(COOH)—C₆H₅ | C₄₀H₄₉NO₅ (623.84) |
| 37 | A | 9 | —NHCH₂—(3-pyridyl) | C₆₄H₈₈N₂O₃ (933.42) |
| 38 | A | 9 | —NHCH₂CH₂—(imidazolyl-NH) | C₆₃H₈₉N₃O₃ (936.43) |
| 39 | A | 2 | —NH—C₆H₄—OH | C₂₉H₃₁NO₄ (457.57) |
| 40 | A | 3 | —NHCH₂CH₂—(imidazolyl-NH) | C₂₈H₃₃N₃O₃ 459.59 |

TABLE 5-A-continued

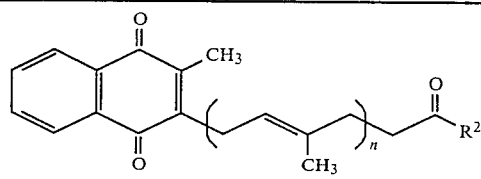

| Product Ia- | Method | n | R² | Molecular formula (Molecular weight) |
|---|---|---|---|---|
| 41 | A | 2 | —NH—⟨piperidine⟩N—CH₃ | $C_{29}H_{38}N_2O_3$ (462.64) |

TABLE 5-B

| Product Ia- | Melting point or NMR spectrum (in CDCl₃, TMS internal standard); δ(ppm) |
|---|---|
| 23 | 113.5–114° C. |
| 24 | 1.56(3H), 1.77(3H), 2.05(7H), 2.30(3H), 2.30(4H), 3.35(2H), 4.60(1H), 5.00(2H), 7.00(1H), 7.40–8.15(4H), 8.82(1H) |
| 25 | 1.57(3H), 1.76(3H), 2.17(3H), 2.32(4H), 3.35(2H), 2.6–2.9(8H), 5.02(2H), 7.4–8.2(4H) |
| 26 | 108–109° C. |
| 27 | 1.55(6H), 1.77(3H), 2.17(3H), 2.32(4H), 3.35(2H), 3.39(2H), 5.05(3H), 5.90(2H), 6.70(2H), 6.80(1H), 7.50–8.20(4H) |
| 28 | 1.55(6H), 1.77(3H), 2.17(3H), 2.33(4H), 3.35(2H), 3.40(2H), 3.80(3H), 3.83(6H), 5.05(3H), 6.55(2H), 7.50–8.20(4H) |
| 29 | 1.58(15H), 1.67(3H), 1.78(3H), 2.17(3H), 2.33(4H), 2.97(2H), 3.35(2H), 5.05(5H), 5.30(1H), 7.50–8.20(4H) |
| 30 | 90–91° C. |
| 31 | 1.55(6H), 1.78(3H), 2.17(3H), 2.29(4H), 3.35(2H) |
| 32 | 1.55(6H), 1.78(3H), 2.17(3H), 2.28(4H), 3.35(2H), 3.60(8H), 5.05(3H), 7.50–8.20(4H) |
| 33 | 1.55(6H), 1.78(3H), 2.17(3H), 2.33(4H), 3.35(2H), 5.05(3H), 6.5–8.2(7H) |
| 34 | 1.55(6H), 1.78(3H), 2.17(3H), 2.33(4H), 2.75(3H), 3.35(2H), 5.05(3H), 6.5–8.2(7H) |
| 35 | 1.58(9H), 1.75(3H), 1.9–2.1(12H), 2.17(3H), 2.27(4H), 3.35(2H), 4.42(2H), 5.10(4H), 6.35(1H), 7.1–8.9(8H) |
| 36 | 1.59(9H), 1.75(3H), 1.9–2.1(12H), 2.17(3H), 2.28(4H), 3.35(2H), 5.10(4H), 7.28(5H), 7.4–8.2(4H) |
| 37 | 1.59(24H), 1.75(3H), 2.0(CH₂), 2.17(3H), 2.27(4H), 3.35(2H), 4.42(2H), 5.10(9H), 6.35(1H), 7.1–8.9(8H) |
| 38 | 1.59(24H), 1.75(3H), 2.0(CH₂), 2.17(3H), 2.28(4H), 3.35(2H), 4.9–5.2(9H), 7.18–8.2(6H) |
| 39 | 1.56(3H), 1.75(3H), 2.17(3H), 2.33(4H), 3.35(2H), 5.02(2H), 6.7–6.9(4H), 7.4–8.2(4H) |
| 40 | 1.57(6H), 1.75(3H), 2.17(3H), 2.30(4H), 3.35(2H), 4.9–5.2(3H), 7.1–8.2(6H) |
| 41 | 1.56(3H), 1.75(3H), 2.17(3H), 2.27(3H), 2.33(4H), 3.35(2H), 5.0(2H), 7.4–8.2(4H) |

TABLE 6-A

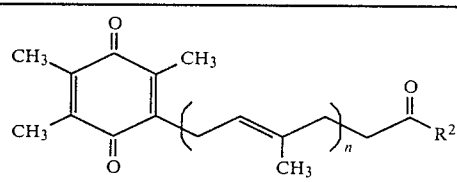

| Product Ia- | Method | n | R² | Molecular formula (Molecular weight) |
|---|---|---|---|---|
| 42 | A | 2 | —NHCH₂—⟨pyridin-3-yl⟩ | $C_{27}H_{34}N_2O_5$ (466.58) |
| 43 | A, B | 2 | —NHNH—⟨3-CF₃-phenyl⟩ | $C_{28}H_{33}N_2O_5F_3$ (534.58) |
| 44 | A, B | 2 | —NHN(CH₃)₂ | $C_{23}H_{34}N_2O_5$ (418.54) |

TABLE 6-A-continued

Structure: 2,3-dimethyl-5,6-dimethyl-1,4-benzoquinone with side chain –(CH$_2$CH=C(CH$_3$)CH$_2$)$_n$–C(=O)R$^2$

| Product Ia- | Method | n | R$^2$ | Molecular formula (Molecular weight) |
|---|---|---|---|---|
| 45 | A | 3 | –N(piperazine)N–(CH$_2$CH=C(CH$_3$)CH$_2$)$_3$H | C$_{45}$H$_{68}$N$_2$O$_3$ (685.01) |
| 46 | A | 3 | –N(piperazine)N–CH$_2$–(3,4,5-trimethoxyphenyl) | C$_{40}$H$_{56}$N$_2$O$_6$ (660.86) |
| 47 | A | 3 | –NH$_2$ | C$_{29}$H$_{37}$NO$_3$ (411.56) |

TABLE 6-B

| Product Ia- | Melting point or NMR spectrum (in CDCl$_3$, TMS internal standard); δ(ppm) |
|---|---|
| 42 | 94–97° C. |
| 43 | 1.59(3H), 1.71(3H), 1.98(9H), 2.0–2.2(4H), 2.35(4H), 3.18(2H), 4.9–5.1(2H), 6.40(1H), 6.9–7.2(4H), 7.96(1H) |
| 44 | 1.59(3H), 1.72(3H), 2.00(9H), 2.0–2.5(8H), 2.50(3H), 2.59(3H), 3.18(2H), 4.9–5.1(2H), 6.26(1H) |
| 45 | 1.58(15H), 1.70(3H), 1.98(9H), 2.0–2.2(CH$_2$), 2.29(4H), 2.97(2H), 3.16(2H), 5.0–5.2(5H) |
| 46 | 1.58(6H), 1.70(3H), 1.98(9H). 2.0–2.2(8H), 2.30(4H), 3.22(2H), 3.50(2H), 3.5–3.8(2H) 3.88(3H), 3.90(6H), 4.00(6H), 4.85–5.3(3H), 6.68(2H) |
| 47 | 1.58(6H), 1.70(3H), 1.98(9H), 2.0–2.2(8H), 2.29(4H), 3.22(2H), 4.9–5.1(2H) |

TABLE 7-A

Structure: trisubstituted benzene with OR$^3$ (×2), CH$_3$, R$^1$ (×2), and side chain –(CH$_2$CH=C(CH$_3$)CH$_2$)$_n$–C(=O)R$^2$

| Product Ib- | Method | n | R$^1$ | R$^2$ | R$^3$ |
|---|---|---|---|---|---|
| 1 | A | 1 | OCH$_3$ | –N(piperazine)N–CH$_2$–(3,4-methylenedioxyphenyl with OCH$_2$) | CH$_2$OCH$_3$ |
| 2 | A | 3 | ″ | ″ | ″ |
| 3 | A, E | 3 | (cyclohexadienyl) | ″ | CH$_3$ |
| 4 | A | 2 | ″ | –NH$_2$ | ″ |

TABLE 7-B

| Product Ib- | Molecular formula (Molecular weight) | NMR spectrum (in CDCl$_3$, TMS internal standard); δ(ppm) |
|---|---|---|
| 1 | C$_{32}$H$_{44}$N$_2$O$_9$ (600.72) | 1.77(3H), 2.16(3H), 2.34 (8H), 3.31(2H), 3.37(2H), 3.4–3.6(4H), 3.57(6H), 3.84 (6H), 4.97 & 5.01(4H), 5.08 (1H), 5.90(2H), 6.70(2H), 6.81(1H) |
| 2 | C$_{42}$H$_{60}$N$_2$O$_9$ | 1.56(3H), 1.60(3H), 1.75 |

TABLE 7-B-continued

| Product Ib- | Molecular formula (Molecular weight) | NMR spectrum (in CDCl₃, TMS internal standard); δ(ppm) |
|---|---|---|
|  | (736.96) | (3H), 1.9-2.1(8H), 2.16(3H), 2.33(4H), 2.38(4H), 3.36 (2H), 3.41(2H), 3.54(3H), 3.56(3H), 3.4-3.6(4H), 3.85 (6H), 4.9-5.2(3H), 5.02 (4H), 5.91(2H), 6.71(2H), 6.82(1H) |
| 3 | C₄₂H₄₄O₅N₂ (656.82) | 1.58(6H), 1.83(3H), 2.33 (3H), 3.38(2H), 3.55(2H), 3.85(6H), 5.10(3H), 5.90 (2H), 6.67(2H), 6.77(1H), 7.20-8.20(4H) |
| 4 | C₂₅H₃₃NO₃ (395.52) | 1.59(3H), 1.83(3H), 2.33 (3H), 3.38(2H), 3.86(6H), 5.1(2H), 7.2-8.2(4H) |

EXAMPLE 6

A quinone compound (IIa, $R^1=OCH_3$, n=2, 376 mg) was dissolved in methylene chloride (5 ml), and DCC (210 mg) and triethylamine (100 mg) were added to the solution, followed by stirring at room temperature for 1 hour. The organic layer was then washed with water, dried (magnesium sulfate) and concentrated. The residue was crystallized from isopropyl ether, resulting in the desired quinone compound (Ia-48, $R^1=OCH_3$,

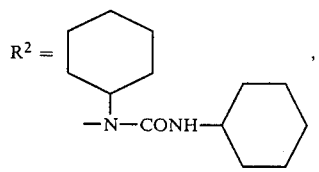

n=2 520 mg), m.p., 113° to 115° C.
$C_{34}H_{50}N_2O_6$(MW: 582.76).

EXPERIMENTAL EXAMPLE 1

Blood-pressure reducing action of the compounds of the present invention

The blood-pressure reducing action of the compounds obtained in the above-mentioned Examples was confirmed with the use of SHR (spontaneously hypertensive rats) in accordance with the method of Watson and Ludden (L. S. Watson & C. T. Ludden in "New Antihypertensive Drugs", A. Scriabin and C. S. Sweet, Ed., Spectrum Publications, New York, 1976, page 87). As a control compound, L-methyldopa was orally administered in a dose of 40 mg/kg, while an equimolar amount of a test compound was orally given, to examine the effect. Results are shown in Table 8, where the marks, (+++), (++), (+) and (±), indicate the blood-pressure reducing actions of 31 to 40 mmHg, 21 to 30 mmHg, 11 to 20 mmHg and not more than 10 mmHg, respectively.

TABLE 8

| Compound | Blood-pressure reducing action |
|---|---|
| L-Methyldopa | +++ |
| IIa-3 | +++ |
| IIa-4 | +++ |
| IIa-5 | +++ |
| IIa-9 | ++ |
| IIa-12 | ++ |
| IIa-13 | ++ |
| IIa-14 | ++ |

TABLE 8-continued

| Compound | Blood-pressure reducing action |
|---|---|
| IIa-15 | ++ |
| IIa-16 | ++ |
| IIa-19 | ++ |
| IIa-20 | ++ |
| IIa-21 | ++ |

EXPERIMENTAL EXAMPLE 2

The inhibitory effect of quinone derivatives on SRS-A (slow reacting substance of anaphylaxis) production and release The inhibitory effect on SRS-A production and release was examined by the method of Orange and Moore (J. Immunol., 116, 392-397, 1976). Quinone derivatives were added to guinea-pig lung fragments sensitised with egg albumin as the antigen, and the amount of SRS-A produced and released as a consequence was assayed by the method of Brocklehust (J. Physiol., 151, 416-435, 1960). The inhibitory effect was shown in Table 9.

TABLE 9

| Compound[1] No. | Concentration (μM) | Inhibitory Effect[2] on SRS-A Production (%) |
|---|---|---|
| IIa-3 | 10 | 38.6 ± 4.3 |
| IIa-4 | 1 | 24.3 ± 4.2 |
| IIa-7 | 10 | 40.2 ± 7.3 |
| IIa-10 | 1 | 35.0 ± 6.3 |
| IIa-12 | 1 | 21.8 ± 8.5 |
| Ia-6 | 1 | 26.8 ± 2.2 |
| Ia-11 | 1 | 15.0 ± 5.6 |
| BW-755c[3] | 10 | 4.7 ± 3.7 |
|  | 100 | 15.3 ± 4.3 |
| BSP[4] | 10 | 18.7 ± 6.6 |
|  | 100 | 50.8 ± 10.7 |

[1]The compound was added as dissolved in ethanol or dimethyl sulphoxide.
[2]The inhibitory effect on SRS-A production was expressed as the % inhibition of production and release of SRS-A.
[3]3-Amino-1-[m-(trifluoromethyl)phenyl]-2-pyrazoline.
[4]Sodium baikalein phosphate.

EXPERIMENTAL EXAMPLE 3

Effects on the suppression of mortal activity of arachidonic acid in mouse by quinone derivatives Male mice (four weeks old, JCL:ICR) were used in this experimental. Quinone derivatives were suspended with arabin to administrate per OS. After one hour of the oral administration at a dose of 300 mg/kg of a quinone derivative, an aqueous solution of arachidonic acid (20 mg/ml, pH 8.8) was intravenously administrated at dose of 60 mg/kg of arachidonic acid from mouse tail vein. The suppressive effects were shown in Table 10 by the ratio of the number of survival mice to the total number of mice administrated the test compound.

TABLE 10

| Compound No. | Number of survival mice/ Total number of mice |
|---|---|
| Ia-3 | 2/5 |
| Ia-6 | 2/5 |
| Ia-7 | 2/5 |
| Ia-9 | 2/5 |
| Ia-11 | 4/5 |
| Ia-22′ | 4/5 |
| Ia-28 | 5/5 |
| Ia-42 | 3/5 |
| Ia-48 | 2/5 |

TABLE 10-continued

| Compound No. | Number of survival mice/Total number of mice |
|---|---|
| IIa-3 | 2/5 |
| Arachidonic acid | 0/5 |

EXAMPLES OF PHARMACEUTICAL COMPOSITION

| (A) Capsule | |
|---|---|
| (1) Compound (IIa-3) | 50 mg |
| (2) Cellulose fine powder | 30 mg |
| (3) Lactose | 37 mg |
| (4) Magnesium stearate | 3 mg |
| Total | 120 mg |

All the materials were mixed and filled into a gelatin capsule.

| (B) Soft Capsule | |
|---|---|
| (1) Compound (Ia-11) | 50 mg |
| (2) Corn starch oil | 100 mg |
| Total | 150 mg |

A mixed solution of (1) and (2) were prepared and filled into a soft capsule by a conventional manner.

| (C) Tablet | |
|---|---|
| (1) Compound (Ia-8) | 50 mg |
| (2) Lactose | 34 mg |
| (3) Corn starch | 10.6 mg |
| (4) Corn starch (gelatinized) | 5 mg |
| (5) Magnesium stearate | 0.4 mg |
| (6) Calcium carboxymethyl cellulose | 20 mg |
| Total | 120 mg |

All the materials were mixed and compressed by a tabletting machine to prepare a tablet in accordance with a conventional manner.

What we claim is:

1. A compound of the formula

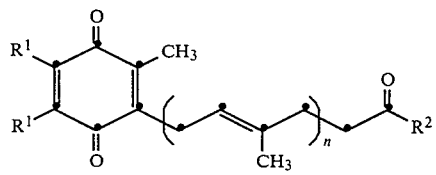

wherein
n is an integer of 1 to 10,
$R^1$ is methyl or methoxy, or two of $R^1$ combine to represent —CH=CH—CH=CH—, and
$R^2$ is (1) amino or (2) a mono- or di-substituted amino group selected from the class consisting of mono- or di-$C_{1-6}$ alkylamino, $C_{3-6}$ cycloalkylamino, $C_{3-6}$ cycloalkyl-$C_{1-3}$ alkylamino, phenyl-$C_{1-3}$ alkylamino, $C_{1-4}$ alkoxyamino and anilino
said mono- or di-substituted amino groups being unsubstituted or substituted by $C_{1-4}$ alkyl, hydroxyl, $C_{1-4}$ alkoxy, $C_{1-4}$ alkylthio, carboxyl, one of mono- to decaprenyl, benzyl, 3,4,5-trimethoxybenzyl or 3,4-methylenedioxybenzyl,
or its hydroquinone form,
or a pharmaceutically acceptable salt thereof.

2. A compound according to claim 1, wherein n is 2 or 3.

3. A compound according to claim 1, wherein $R^1$ is methoxy.

4. A compound according to claim 1, wherein the mono- or di-substituted amino group as $R^2$ is mono- or di-$C_{1-6}$ alkylamino, phenyl-$C_{1-3}$ alkylamino, $C_{1-4}$ alkoxyamino or anilino,
said mono- or di-substituted amino group being unsubstituted or substituted by $C_{1-4}$ alkyl, hydroxyl, $C_{1-4}$ alkoxy, $C_{1-4}$ alkylthio or carboxyl.

5. A compound according to claim 4, wherein the mono- or di-substituted amino group is anilino, 2- or 4-hydroxyphenylamino or 3,4-dihydroxyphenylamino.

6. The compound according to claim 1, wherein n is 2, $R^1$ is methoxy, and $R^2$ is 4-hydroxyphenylamino.

7. The compound according to claim 1, wherein n is 2, $R^1$ is methoxy and $R^2$ is amino.

8. A compound according to claim 1, said compound being 2,3-dimethoxy-5-methyl-6-(5-methylaminocarbonyl-3-methyl-2-pentenyl)-1,4-benzoquinone.

9. A compound according to claim 1, said compound being 2,3-dimethoxy-5-methyl-6-(9-isopropylaminocarbonyl-3,7-dimethyl-2,6-nonadienyl)-1,4-benzoquinone.

10. A compound according to claim 1, said compound being 2-(41-aminocarbonyl-3,7,11,15,19,23,27,31,35,39-decamethyl-2,6,10,14,18,22,26,30,34,38-hentetracontadecaenyl)-3-methyl-5,6-dimethoxy-1,4-benzoquinone.

11. A pharmaceutical composition which comprises as an active ingredient an effective amount of a compound of the formula:

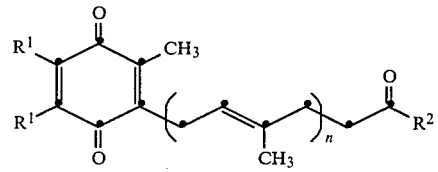

wherein
n is an integer of 1 to 10,
$R^1$ is methyl or methoxy, or two of $R^1$ combine to represent —CH=CH—CH=CH—, and
$R^2$ is (1) amino or (2) a mono- or di-substituted amino group selected from the class consisting of mono- or di-$C_{1-6}$ alkylamino, $C_{3-6}$ cycloalkylamino, $C_{3-6}$ cycloalkyl-$C_{1-3}$ alkylamino, phenyl-$C_{1-3}$ alkylamino, $C_{1-4}$ alkoxyamino and anilino
said mono- or di-substituted amino groups being unsubstituted or substituted by $C_{1-4}$ alkyl, hydroxyl, $C_{1-4}$ alkoxy, $C_{1-4}$ alkylthio, carboxyl, one of mono- to decaprenyl, benzyl, 3,4,5-trimethoxybenzyl or 3,4-methylenedioxybenzyl,
or its hydroquinone form,
or a pharmaceutically acceptable salt thereof,
in association with a pharmaceutically acceptable carrier or excipient.

12. A method for the treatment of allergosis in a mammal which comprises administering to said mammal an effective amount of a compound of the formula:

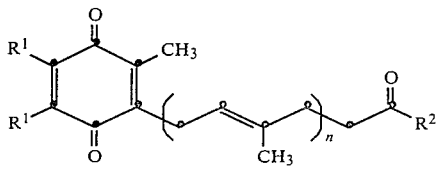

wherein
n is an integer of 1 to 10,
R¹ is methyl or methoxy, or two of R¹ combine to represent —CH=CH—CH=CH—, and R² is (1) amino or (2) a mono- or di-substituted amino group selected from the class consisting of mono- or di-$C_{1-6}$ alkylamino, $C_{3-6}$ cycloalkylamino, $C_{3-6}$ cycloalkyl-$C_{1-3}$ alkylamino, phenyl $C_{1-3}$ alkylamino, $C_{1-4}$ alkoxyamino and anilino said mono- or di-substituted amino groups being unsubstituted or substituted by $C_{1-4}$ alkyl, hydroxyl, $C_{1-4}$ alkoxy, $C_{1-4}$ alkylthio, carboxyl, one of mono- to decaprenyl, benzyl, 3,4,5-trimethoxybenzyl or 3,4-methylenedioxybenzyl, or its hydroquinone form,
or a pharmaceutically acceptable salt thereof.

* * * * *